United States Patent [19]

Taniguchi et al.

[11] Patent Number: 5,173,719
[45] Date of Patent: Dec. 22, 1992

[54] METHOD AND APPARATUS FOR THE INSPECTION OF PATTERNS

[75] Inventors: Yuzo Taniguchi, Higashimurayama; Tooru Fukui, Hamura; Mikihito Saito, Tokyo; Yoshiichi Hori, Kodaira; Takahiro Kamagata, Honmachi, all of Japan

[73] Assignees: Hitachi, Ltd.; Hitachi Tokyo Electronics Co., Ltd., both of Tokyo, Japan

[21] Appl. No.: 630,190

[22] Filed: Dec. 19, 1990

[30] Foreign Application Priority Data

Dec. 20, 1989 [JP] Japan .................................. 1-330222
Nov. 29, 1990 [JP] Japan .................................. 2-332608

[51] Int. Cl.⁵ ...................... G01B 11/00; G01N 21/00
[52] U.S. Cl. ..................................... 356/394; 356/237
[58] Field of Search .................. 356/237, 394, 398; 250/572; 382/8, 22; 358/101, 106, 107

[56] References Cited

U.S. PATENT DOCUMENTS 4,547,895 10/1985 Mita et al. ............................ 356/387
4,603,974 8/1986 Matsui ................................. 356/394

FOREIGN PATENT DOCUMENTS

59-192943 11/1984 Japan .
63-52434 3/1988 Japan .

Primary Examiner—Richard A. Rosenberger
Assistant Examiner—Hoa Pham
Attorney, Agent, or Firm—Fay, Sharpe, Beall, Fagan, Minnich & McKee

[57] ABSTRACT

The present invention relates to a technique, in the inspection of a defect of a semiconductor memory or the like, in which chip comparison is separated from repetitive pattern comparison in a region of a wafer to be inspected whereby both the comparisons are rendered possible to perform in parallel in one and the same scanning.

17 Claims, 7 Drawing Sheets

METHOD AND APPARATUS FOR THE INSPECTION OF PATTERNS

BACKGROUND OF THE INVENTION

The present invention relates to the pattern inspection technology, and namely, to the technology which is effectively applied to failure inspection for patterns of semiconductor wafers, photomasks, magnetic disks, photo disks and the like, and particuarly to pattern or defect inspection for integrated circuit devices having both period pattern and random pattern in a single chip area of a VLSI memory or a CCD (Charge Coupled Device) or the like.

As a conventional pattern inspection method, a system for comparing two adjacent chips has been heretofore widely used as an appearance inspection apparatus for a photomask or a wafer. In addition, as a defect detection method for a wafer having a complicated multi-layer pattern, a method for repeatedly comparing patterns has been proposed as disclosed in Japanese Patent Application Laid-Open Publication No. 59-192943 (1984).

The two-chip comparison inspection compares patterns of two adjacent chips, and has, in case of a semiconductor wafer having a multilayer pattern, a problem that detection of a minute defect is difficult due to the difference in pattern dimension, overlapping accuracy of patterns and the like by chips. On the other hand, the repeated pattern comparison method compares patterns nearby, and a difference between the patterns compared is small and even a minute defect can be detected, but there is a problem that only the repeated pattern portion can be inspected.

In case of a wafer pattern which is to be inspected, a fine pattern portion is different from a relatively thick pattern in size of an interior defect, and accordingly, the sensitivity of detection required is also different.

Therefore, the present inventors have proposed a method for switching the sensitivity of detection by a pattern to be inspected, as disclosed in Japanese Patent Application Laid-Open Publication 63-52434 (1988).

Furthermore, as an inspection apparatus for carrying out both two-chip comparison and repeated pattern comparison, a Wafer Appearance Inspection Apparatus KLA-20 Series made by KLA limited, U.S.A. has been proposed. According to this apparatus, repeated patterns and random patterns can be separately inspected.

BRIEF SUMMARY OF THE INVENTION

Since the art disclosed in the aforementioned Japanese Patent Application Laid-Open Publication No. 63-52434 (1988) is based on the premise that 2-chip comparison inspection takes a multilayer pattern poses a problem.

On the other hand, the apparatus of the aforementioned type made by KLA Ltd., U.S.A., compares images introduced by iTV (industrial Television) and poses a problem that since movement and stop of the stage are repeated, the inspection speed is slow. Moreover, since the repeated pattern area and the random pattern area are separately inspected, in the case where an unrepeated pattern is present in a small area within the repeated pattern area, there is a problem that even if that area is extremely fine, that portion still has to be separately subjected to 2-chip comparison.

Accordingly, in the aforementioned prior arts, no consideration has been taken to simultaneously solve the improvement of detection sensitivity and improvement of inspection speed.

A first object of the present invention is to provide a pattern defect inspection technology which can simultaneously realize the improvement of detection sensitivity and improvement of inspection speed.

A further object of the invention is to provide an inspection technology adopted to defect a defect in an inspection of a high integrated semiconductor integrated circuit memory and wafer.

Another object of the invention is to provide a signal processing circuit for a defect inspection apparatus capable of executing the locating of a defect with high speed and high precision.

Still another object of the invention is to provide a defect inspection apparatus which can independently set various patterns for chip comparison and repeated pattern comparison.

The above and other objects and new features of the present invention will become apparent from the ensuing description of the present specification and the accompanying drawings.

Of the inventions disclosed in the present application, a typical one will be briefly described hereinafter.

That is, in the method and apparatus for inspection of pattern defects according to the present invention, generally, repeated pattern portions such as a memory cell area of a memory having fine patterns or light receiving areas of photosensor elements such as CCD, MID (Mos Image Device), etc. and peripheral circuit portions are inspected by separate circuits whereby repeated pattern comparison inspection of relatively good detection sensitivity can be applied to the repeated pattern portions. In addition, inspection is carried out while continuously scanning a stage effective for carrying out high speed inspection. Defect outputs of the respective chip comparison and repeated pattern comparison are not duplicated in areas of inspection prepared on the basis of pattern arrangement information within the chips, and the high speed inspection is rendered possible.

According to the aforementioned system, a portion formed with fine patterns such as a memory cell within a wafer and requiring the inspection with high sensitivity can be inspected with high sensitivity. A relatively large pattern portion such as the periphery of the chip can be inspected with relatively low sensitivity to render possible the defect detection with detection sensitivity according to the fineness of patterns within the chip. Moreover, the aforesaid objects of providing a pattern defect inspection apparatus capable of providing high speed inspection can be achieved.

DETAILED DESCRIPTION OF THE INVENTION

Figure 1:
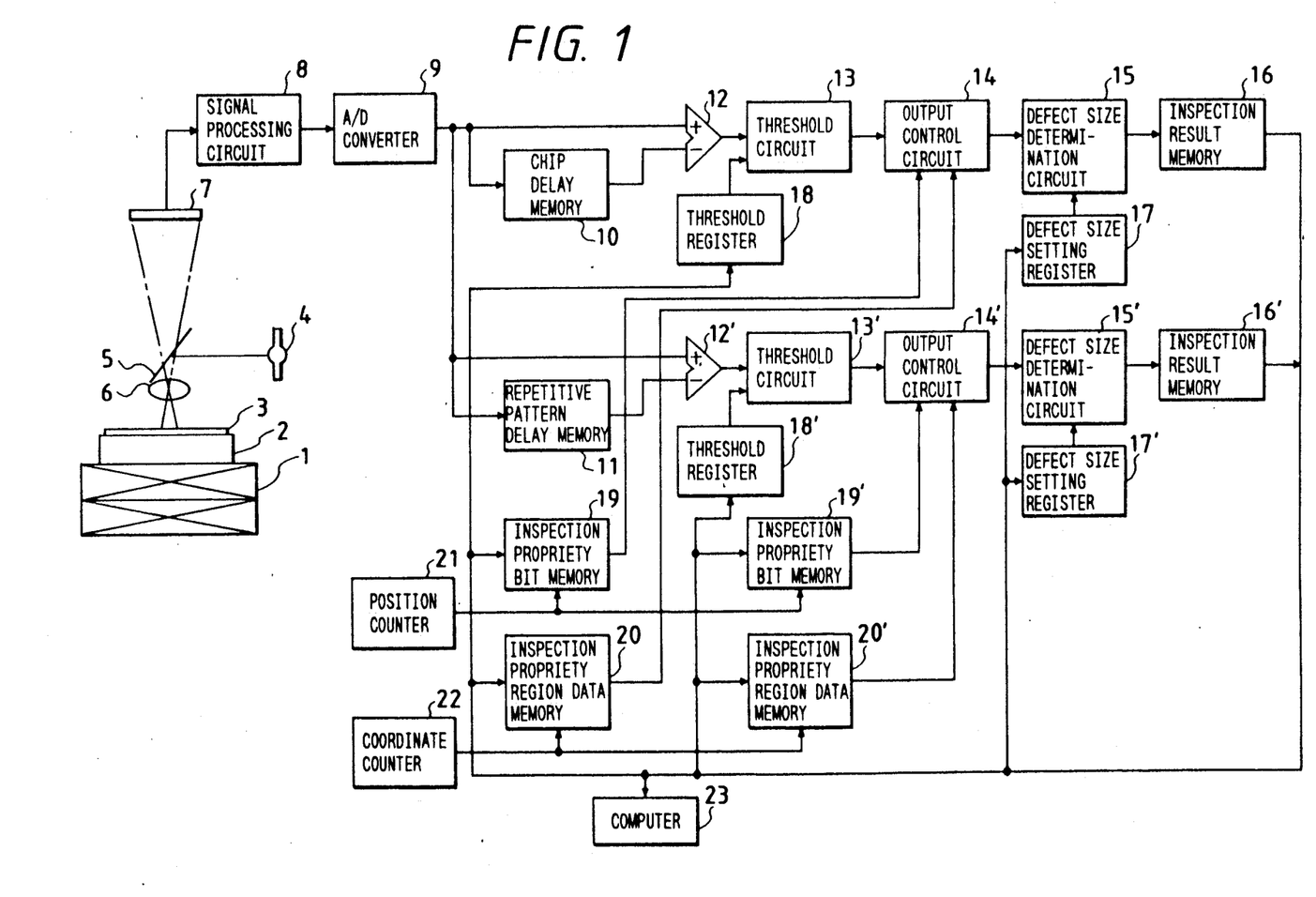
FIG. 1 is an explanatory view showing one embodiment in which the present invention is applied to a wafer appearance inspection.

FIG. 1 is an explanatory view showing one embodiment of a pattern defect inspection apparatus which is one embodiment of the present invention.

The pattern defect inspection apparatus is designed so that a semiconductor wafer 3 fixed on a wafer place bed 2 on a stage 1 formed from an XY table is moved in the X and Y directions by the stage 1 so as to inspect for defects in of the pattern on the wafer 3.

Light from a light source 4 positioned above the wafer 3 is irradiated on the wafer 3 through a half mirror 5 and an objective lens 6, and reflected light from the wafer 3 is enlarged by the objective lens 6 and condensed on a one dimensional optical element (for example, a line sensor such as one dimensional CCD) 7. An electric output of the one dimensional optical element 7 is converted into a light and dark signal of poly-gradations by means of an A/D (Analog/Digital) converter 9 via a signal processing circuit 8 for amplifying a signal or adjusting the signal level.

The light and dark signal of poly-gradations is stored in a chip delay memory 10 for storing an image signal for one chip portion. A differential between a signal output delayed by one chip portion by the chip delay memory 10 and a signal not delayed is taken by a comparator 12, which differential is compared with a set value of a threshold register 18 in which a predetermined threshold of light and dark differential is set by a threshold circuit 13. If the light and dark differential is above the threshold, it is outputted as a possible defect signal from the threshold circuit 13.

This signal is outputted only when a defective output is enabled by an output control circuit 14 for chip comparison and inspection, and a defect larger than a fixed size is stored in an inspection result memory 16 by a defect size determination circuit 15. Defect information stored in the inspection result memory 16 can be data read into a computer 23. A flow of the defect output of the chip comparison and inspection has been described above.

Next, a flow of the defect output of the repeated pattern comparison and inspection will be described hereinafter. The procedure followed to the output of the A/D converter 9 in FIG. 1 is the same as the aforesaid chip comparison and inspection. One of the outputs of the A/D converter 9 is stored in a repetitive pattern delay memory 11 for storing image data of a repetitive pitch portion of a pattern. A differential between the signal output delayed by one repetitive portion of the pattern by the repetitive pattern delay memory and the signal not delayed is taken by a comparator 12', and the differential is compared with a set value of a threshold circuit 13' in which a predetermined light and dark threshold is set. If a light and dark difference is above the threshold, it is outputted as a possible defect signal by the threshold circuit 13'.

This signal is outputted only when a defect output is enabled by an output control circuit 14' for comparison and inspection of a repetitive pattern, and a defect larger than a fixed size is stored into an inspection result memory 16' by a defect size determination circuit 15'. Defect information stored in the inspection result memory 16' can be data read by a computer 23.

Since light and dark threshold registers 18 and 18' for judging the defect detection can be independently set with data from the computer 23, the chip comparison and repetitive pattern comparison can be made from separate thresholds.

Since defect size setting registers 17 and 17' for setting a threshold having a size of defect can be independently set with data from the computer 23, the defect detection sizes of the chip comparison and the repetitive pattern comparison can be separated.

Reference numeral 21 designates a line sensor position counter for counting the bit position in the scanning direction of the line sensor or one dimensional optical element 7; 19, a line sensor inspection propriety bit memory for storing the inspection propriety of bits of the line sensor in the chip comparison and inspection; and 19', a line sensor inspection propriety bit memory for storing the inspection propriety of bits of the line sensor in the repetitive pattern comparison. These line sensor inspection propriety bit memories 19 and 19' can receive data from the computer 23.

Reference numeral 22 designates a coordinate counter in the scanning direction of the stage. Reference numerals 20 and 20' designate inspection propriety region data memories in chips for storing the inspection propriety region in the scanning direction of the stage in the chip comparison and repetitive pattern comparison, respectively. These inspection propriety region memories 20 and 20' can receive data from the computer 23. Outputs of the data memories 19, 19' and 20, 20' are supplied to the inspection output control circuits 14 and 14' to select one of the defect output of the chip comparison and the defect output of the repetitive pattern comparison.

Next, the concept of the division between the chip comparison region and the repetitive pattern comparison region will be described with reference to FIGS. 2, 3 and 4.

Figure 2:
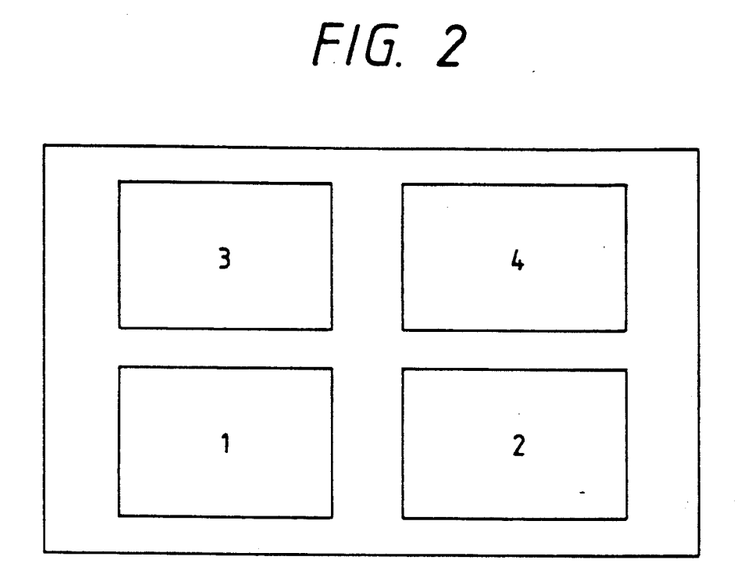
FIG. 2 is a view showing an example of a chip.

FIG. 2 shows an example of a semiconductor memory chip. In FIG. 2, regions 1 to 4 comprise a repetitive pattern portion, namely, a memory cell portion and random pattern portions, namely, peripheral circuit portions.

Figure 3:
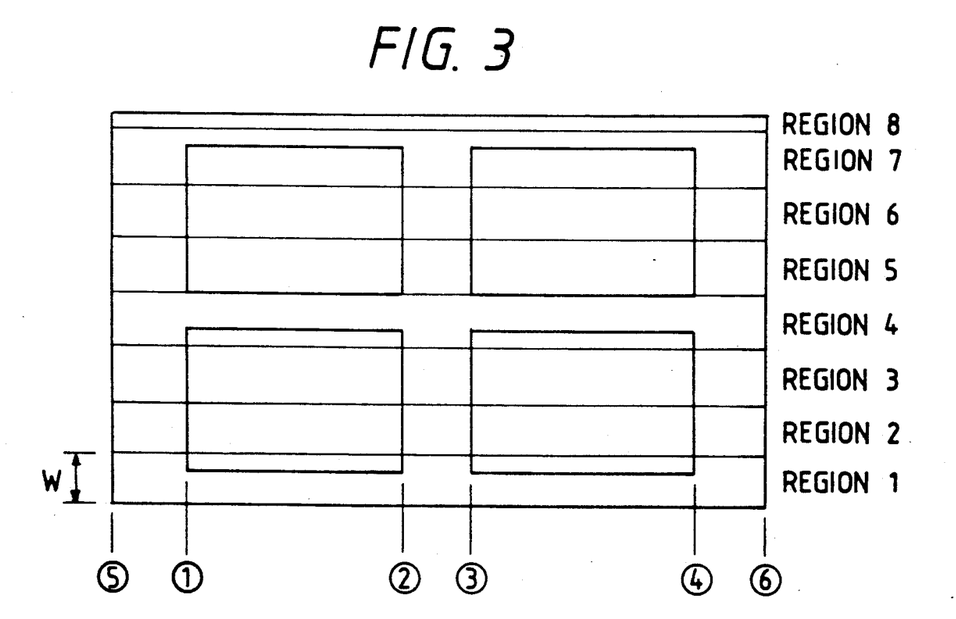
FIG. 3 is an explanatory view in which the chip is divided into scanning width units of a line sensor.
Figure 4:
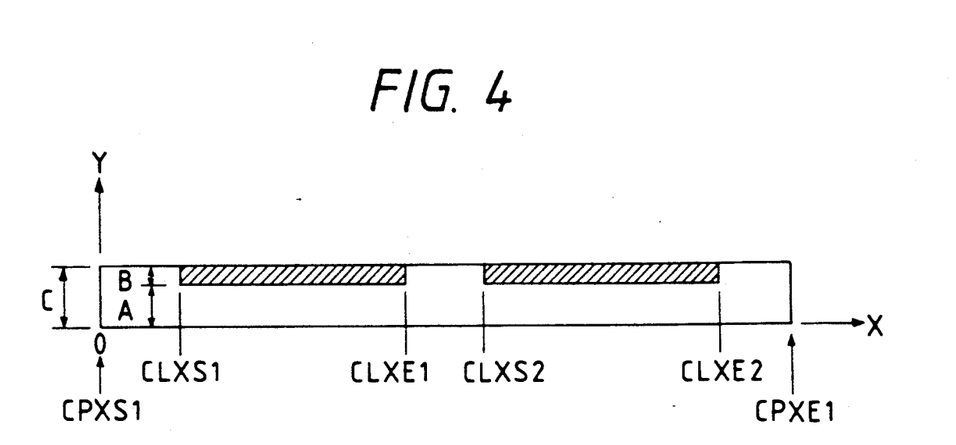
FIG. 4 is an explanatory view showing an area to be compared and inspected with one area in FIG. 3 extracted.

In the case where chips as in FIG. 2 are inspected by the line sensor, the chip is divided, with an effective inspection width (indicated at W in the figure) of the line sensor, into regions 1 to 8 as shown in FIG. 3. In carrying out inspection, first, only the portion of the region 1 of each chip within the wafer is compared and inspected, and after the comparison and inspection of the region 1 has been terminated, comparison and inspection of the regions 2 to 8 are sequentially executed.

As for one example, in this case, if a one dimensional line sensor of 1024 bits is used to take an image with 0.25 $\mu$m/bit, the width W is approximately 250 $\mu$m.

As one example, an inspection propriety area of the chip comparison and repetitive pattern comparison, in case of inspecting the region 1 in FIG. 3, will be described with reference to FIG. 4. A repetitive pattern portion is indicated by the hatched line in FIG. 4. In FIG. 4, the region subjected to chip comparison inspection is CPXS1 $\leq$ X $\leq$ CPXE1, and Y indicates the region in C except the hatched line portion. The region subjected to repetitive pattern comparison is CLXS1≦X≦CLXE1 or CLXS2≦X≦CLXE2, and Y indicates the region in B.

One embodiment for realizing the region control will be described with reference to FIGS. 5 and 6.

Figure 5:
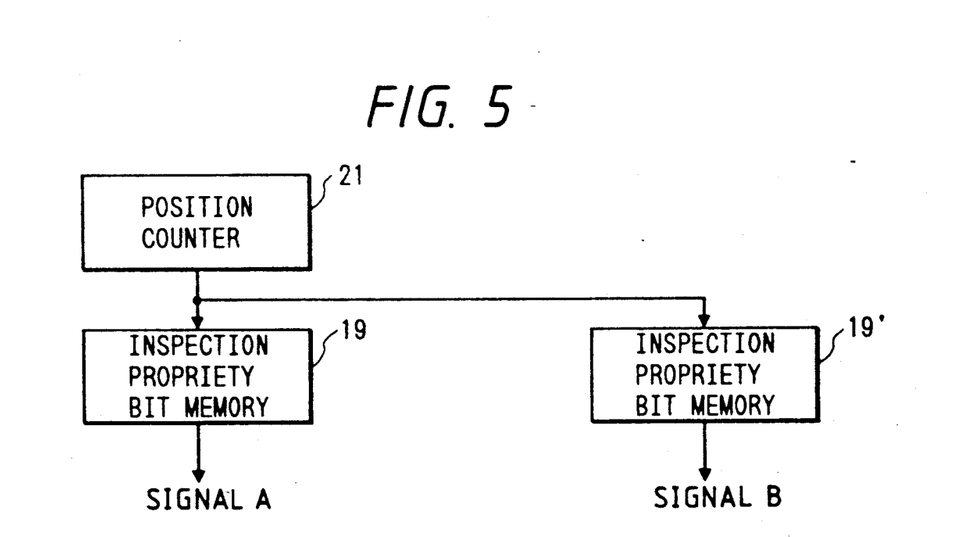
FIG. 5 shows an example of a circuit for controlling an inspection propriety bit in a scanning direction of a line sensor.

FIG. 5 shows the bit location of a line sensor for carrying out a continuous scanning showing a portion of an inspection propriety signal generating circuit of Y. A line sensor position counter 21 designates addresses of inspection propriety bit memories 19 and 19' (memory 19 is for chips, and memory 19' is for repetitive patterns) in which the inspection propriety of bits of the line sensor is stored, and determination is made whether outputs (In FIG. 5, signal A and signal B) of the bit memories 19 and 19' are 1 or 0.

Figure 6:
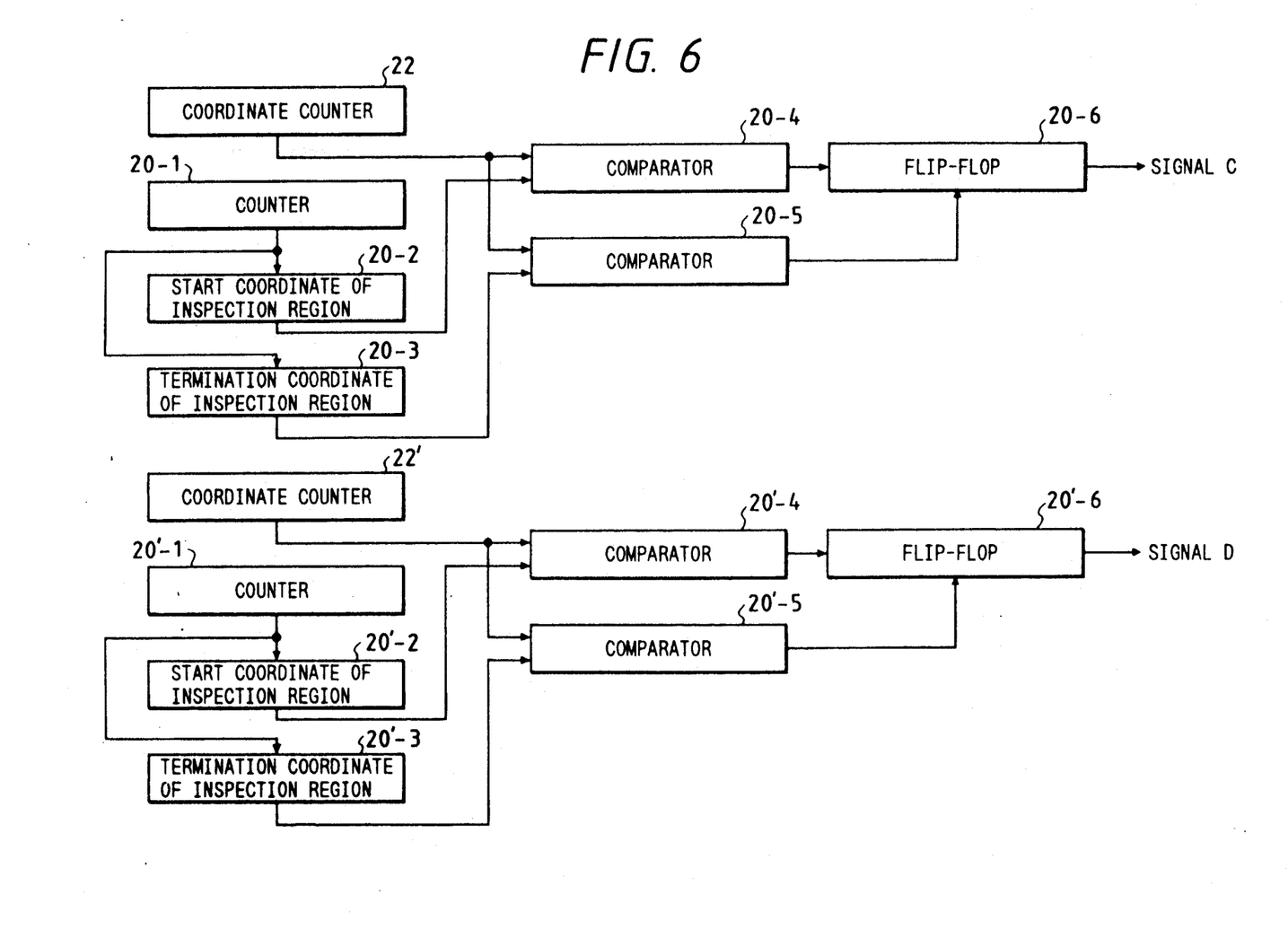
FIG. 6 is a circuit for controlling an inspection area in a stage scanning direction.

Next, FIG. 6 shows a portion of an inspection region data control circuit in a scanning direction of the stage.

In FIG. 6, reference numerals 22 and 22' designate coordinate counters in a scanning direction of the stage. Since the inspection region is in a chip unit, coordinates within the chip are counted, which is reversible according to the scanning direction of the stage. In FIG. 6, reference numerals 20-1 to 20-6 and 20'-1 to 20'-6 show details of portions of the inspection propriety region data memories 20 and 20' in FIG. 1.

Reference numerals 20-1 and 20'-1 designate counters which show in what order the inspection region is, which is reversible according to the scanning direction of the stage. An initial value may be written from the computer 23. Reference numeral 20-2 designates a start coordinate of an X inspection region for comparison, that is, a memory which stores CPXS1 in the FIG. 4 example. Reference numeral 20-3 designates a termination coordinate of an X inspection region for chip comparison, that is, a memory which stores CPXE1 in the FIG. 4 example. In this example, there is only one inspection region for X but a plurality of regions may be set for increasing generalization.

Memory addresses of the coordinates 20-2 and 20-3 are read by the counter 20-1 which shows in what order the inspection region is to designate the addresses. Reference numerals 20-4 and 20-5 designate comparators, which compare the coordinate counter 22, the inspection region start coordinate (output of 20-2) and inspection region termination coordinate (output of 20-3). Reference numeral 20-6 designates a flip-flop, which is set by the output of the comparator 20-4, for example, that is, whether or not entry into the inspection region is made, and which is reset by output of the comparator 20-5, that is, whether or not the inspection region is terminated, output signal C being a control signal.

In FIG. 6, the structure and function of elements 22', 20'-1 to 20'-6 are the same as those of the aforementioned elements 22, 20-1 to 20-6, which are for comparison of repetitive patterns. In the FIG. 4 example, CLXS1 and CLXS2 are stored in 20'-2. In the FIG. 4 example, CLXE1 and CLXE2 are stored in termination coordinate 20'-3. Output signal D of flip-flop 20'-6 constitutes a control signal in a scanning direction of the stage for comparison of repetitive patterns.

In the following, a description will be made of how the logic of circuits 14 and 14' shown in FIG. 1 is realized in connection with signals A, B, C and D shown in FIGS. 5 and 6.

Figure 7:
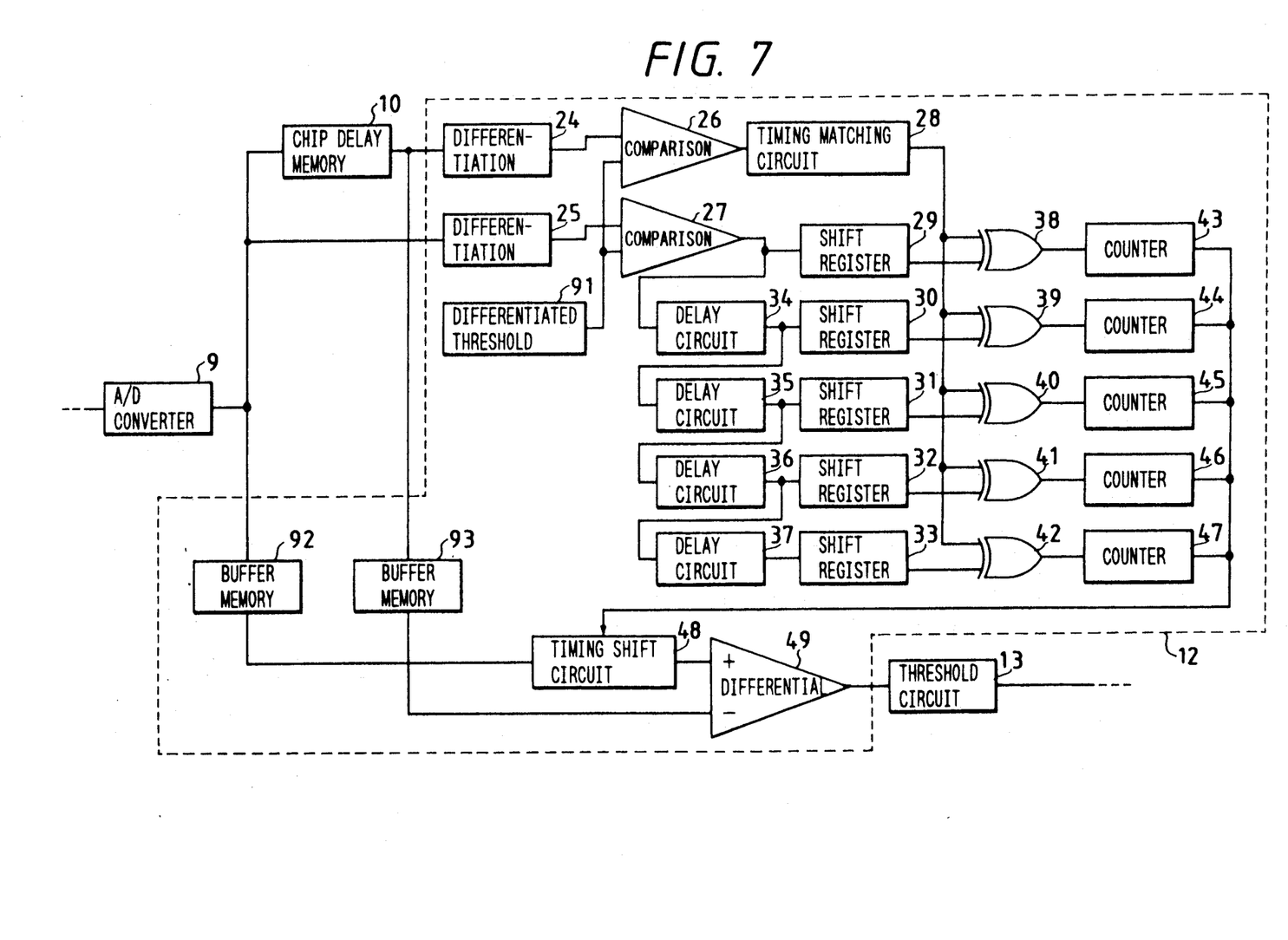
FIG. 7 is a circuit block diagram showing the details of an internal processing of a comparator (on the chip comparison side)

Assume now that for signals A and B, in case of 1, an inspection able bit is present and in case of 0, an inspection disable bit is present; and in signals C and D, in case of 1, within inspection region, and in case of 0, outside inspection region. Then, in case of the output control circuit 14' for repetitive pattern comparison and inspection, the logical formulae are as follows:

$B \times D = 1$: inspection output abled $B \times D = 0$: inspection output disabled In case of the output control circuit 14 for chip comparison and inspection, the logical formulae are as follows:

$(A \times C) \times \overline{(B \times D)} = 1$: inspection output abled $(A \times C) \times \overline{(B \times D)} = 0$: inspection output disabled FIG. 7 is a circuit block diagram showing the details of the internal processing of the comparator 12 (FIG. 1) in the chip comparison and inspection circuit. In FIG. 7, reference numerals 24 and 25 designate differentiators for executing digital second order differentiation to stress the offset portion or the like; 26 and 27, comparators for outputting a "1" as a binary signal for only signals above the threshold of the differential signals and "0" for signals other than those just mentioned; 91, a differential threshold setting circuit for setting thresholds; 29 to 33, 4-bit shift registers; 34 to 37, X-direction signal delay circuits for delaying one column portion of the line sensor 7; 28, a timing matching circuit having a 2-bit shift register connected in series which is operated in the same timing as that of two delay circuits 34 and 35 and shift registers 30 and 31; 38 to 42, coincidence detection circuits for outputting "1" only when two input binary signals are coincided; 43 to 47, counters for counting the coincided number to output data thereof; 48, a positioning circuit for shifting present detection image signals so as to provide the highest coincidence rate on the basis of the coincided data; 49, are subtractor for taking a differential between the present detection image signal and the chip delay image signal; and 92 and 93, buffer memories for retaining image data till positioning has been completed.

Figure 9:
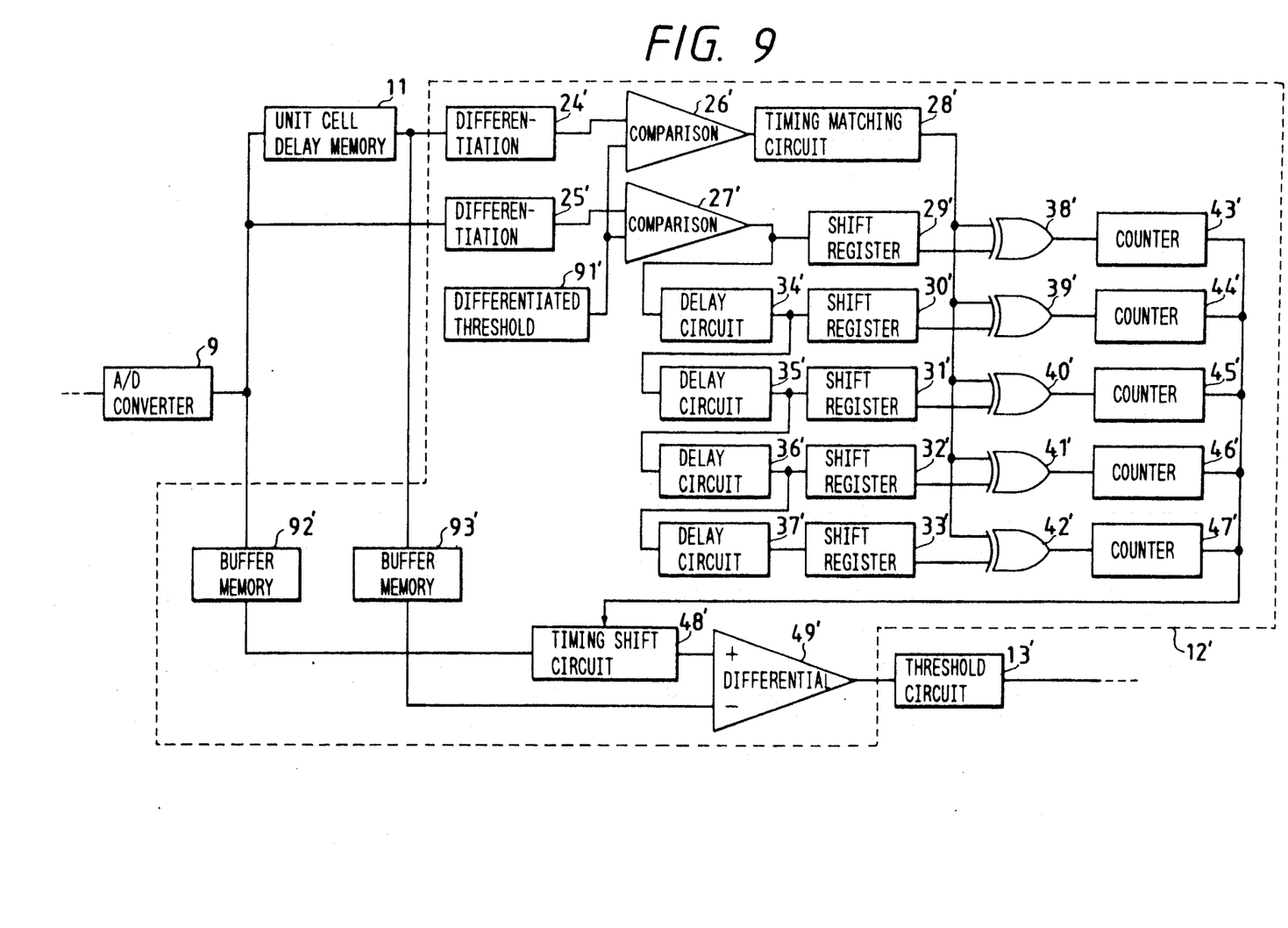
FIG. 9 is a circuit block diagram showing the details of an internal processing of a comparator (the repeated pattern comparison or cell comparison side).

FIG. 9 is a circuit block diagram showing the details of internal processing of the comparator 12' (FIG. 1) in the repetitive pattern comparison and inspection circuit. In FIG. 9, reference numerals 24' and 25' designate differentiators for executing digital second order differentiation to stress offset portions or the like; 26' and 27', comparators for outputting a "1" as a binary signal for only signals above the threshold (the threshold can be set independently of 27) of the differential signals and "0" for signals other than those just mentioned; 91', a differential threshold setting circuit for setting thresholds; 29' to 33', 4-bit shift registers; 34' to 37' X-direction signal delay circuits for delaying the one column portion of the line sensor 7; 28', a timing matching circuit having a 2-bit shift register connected in series which is operated in the same timing as that of two delay circuits 34' and 35' and shift registers 30' and 31'; 38' to 42', coincidence detection circuits for outputting "1" only when two input binary signals are coincided; 43' to 47', counters for counting the coincided number to output data thereof; 48', a positioning circuit for shifting present detection image signals so as to provide the highest coincidence rate on the basis of the coincided data; 49', a subtractor for taking a differential between the present detection image signal and the chip delay image signal; and 92' and 93', buffer memories for retaining image data till positioning has been completed.

Figure 8:
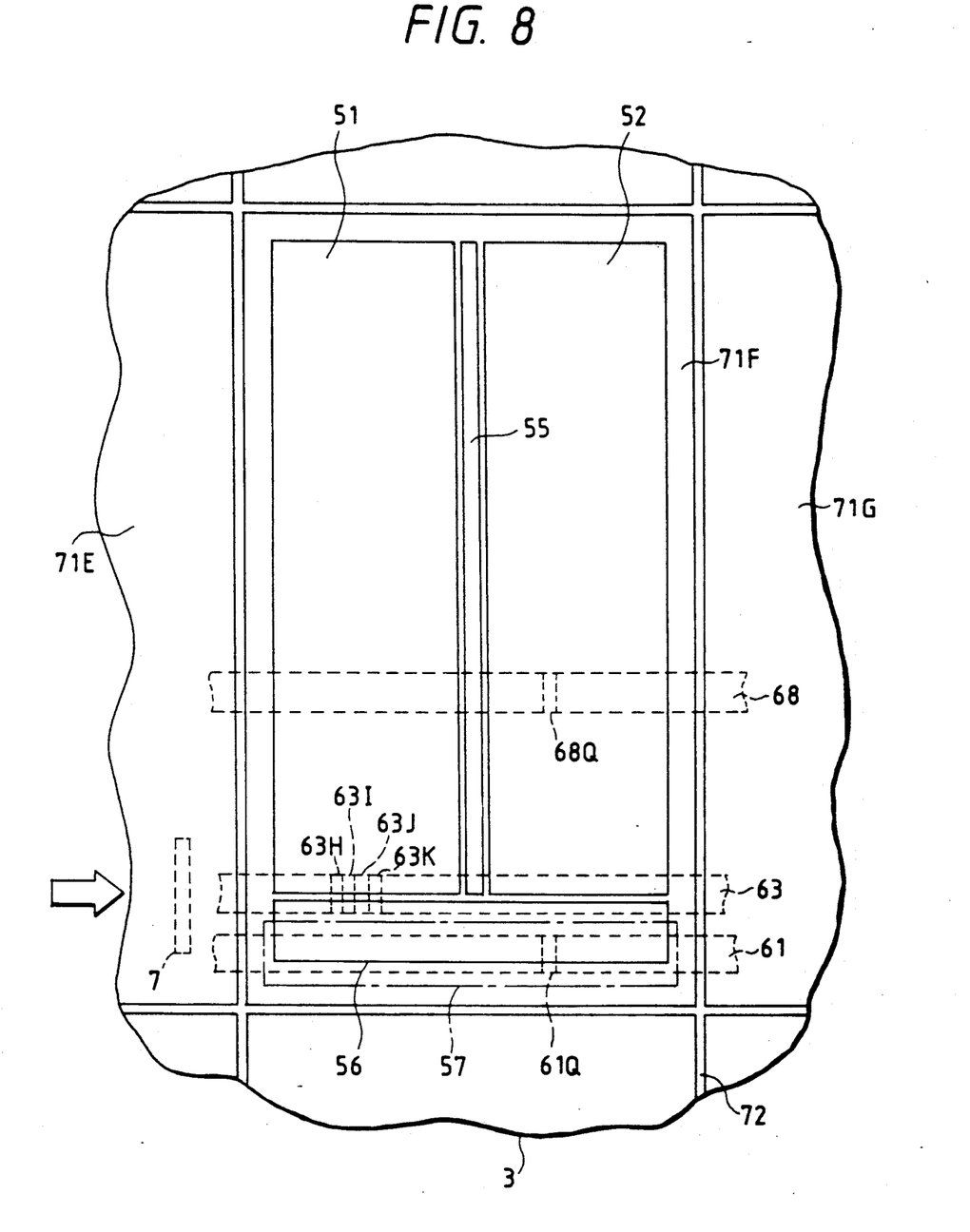
FIG. 8 is a wafer top view of a semiconductor memory device wafer to be inspected.

FIG. 8 is a top view of a wafer for explaining the defect inspection of a semiconductor memory wafer. In FIG. 8, reference numeral 72 designates a scribe line; 71E, a memory chip region precedently scanned; 71F, a chip region being now scanned; 71G, a chip region to be scanned next; 51 and 52, memory cell mat regions comprising repetitive patterns; 55 and 56, peripheral circuits comprising random patterns; 57, an Al power source main wiring zone having a width of approximately 50 μm to 100 μm; 61, 63 and 68, scanning zones which are the same as the zones 1 to 8; and 61Q, 63H to 63K and 68Q, positioning unit regions of the respective scanning zones. The size of the positioning unit region has a length of 256 μm in Y-axis direction (the extending direction of the line sensor) and a length of 64 μm in the X direction, wherein the size of a picture element is 0.25 μm and a line sensor has 1024 bits.

The positioning operation will be described hereinafter with reference to FIGS. 7 and 8. Here, an Al wiring pattern is taken as an example for explanation. For example, a 4M bit DRAM is taken as an example. Since a fatal defect size of a cell portion is different from that of a peripheral portion, it is necessary for the minimum defect sizes in defect size setting registers 17 and 17' to take values different from each other. Furthermore, infrequently, the size of hillock to be a noise of defect detection is also generally different between a thin Al wiring of the cell region and a thick wiring such as a peripheral Al main wiring 57. Accordingly, in the previous example of 4M bit DRAM, the minimum defect size of the chip comparison is set to 0.75 μm, and the minimum defect size of the repetitive pattern comparison is set to 0.5 μm.

In the present apparatus, as described previously, the determination of a defect is executed at real time while continuously reading images so that the wafer is embedded in the scanning one of width 256 μm. In the continuous reading of images and determination of defects, it is necessary to execute the positioning between the read image as a reference and the read image to be inspected at many points on the scanning path at real time. If, for example, a scanning zone 63 is taken as an example, the scanning zone is sub-divided into unit positioning regions 63H to 63K, and positioning is executed every region. On the other hand, in case of the cell comparison, the length in the X direction of the positioning unit region is a repetitive unit length or its integer times. Others are exactly the same except that parameters of the differential threshold value and threshold circuit 13' and defect size register 17' can be set independently of the chip comparison circuit. More specifically, image data in each positioning unit region is stressed in pattern offset by differential operation, that is digitally compared with a similar offset stressed pattern, and they are shifted or positioned on the memory by the timing shift circuits 48 and 48' so as to be best coincided at each positioning unit region, in which state, data are outputted to differentiators or subtractors 49 and 49', whereby they are output as differential signals.

In this manner, image reading, chip comparison, cell comparison and determination thereof are simultaneously executed to select comparison specifications to be outputted by the inspection regions, and therefore, accurate positioning can be made with respect to any mode of patterns.

Furthermore, since various parameters can be set independently by a plurality of inspection circuits, it is possible to inspect at high speeds complicated patterns of semiconductor memories or the like different in parameter of defect in each region.

While in the foregoing, the invention accomplished by the present inventors have been described with reference to the embodiments, it is to be noted needless to say that the present invention is not limited to the above-described embodiments but can be variously modified without departing from the subject matter thereof.

For example, in the above-described embodiments, outputs of comparison and inspection are controlled by the hard ware. However, a detected defect is divided into a repetitive pattern portion and a random pattern portion under the coordinate within the chip thereof, and they may be processed by the soft ware so that the defect data are not duplicated. The threshold of the defect size can also be judged and processed by the soft ware from the coordinate.

Moreover, in the case where the inspection condition of 2-chip comparison is different from the inspection condition of repetitive pattern comparison, soft-ware processing within the computer 23 is carried out to determine an output from which comparator, and the determined result data can be added to the inspected result data. Thereby, it can be judged so that the inspected results under different inspection conditions are obtained. Thus, for example, separate processings can be made in the case where a large amount of inspected result data of many wafers are collected and distribution states by size of defect are statistically processed by other computers or the like.

While in the above-described invention, a description has been made of the case where the invention accomplished by the present inventors is applied to the wafer appearance inspection apparatus in the field of utilization constituting the background thereof, it is to be noted that the present invention is not limited thereto but it can be also applied to an appearance inspection apparatus for, for example, a photomask, a liquid crystal, a disk or the like. It can be also applied to a foreign-matter inspection apparatus for carrying out comparison inspection.

Effects obtained by the typical invention out of the inventions disclosed in the present application will be briefly described as follows:

In the appearance inspection of wafers or the like, the detection sensitivity can be adequately set according to the position within the chip to optimize the detection sensitivity of defects. In addition, since the chip comparison and the repetitive pattern comparison can be simultaneously inspected, the inspection can be made at high speed. In other words, according to the present invention, improvement in detection sensitivity in the pattern defect inspection and improvement in inspection speed can be realized.

What is claimed is:

1. A pattern inspection method characterized by executing a chip comparison inspection for comparing patterns of two chips adjacent to each other on a body to be inspected while keeping pace with a repetitive pattern comparison inspection for comparing the same patterns of the same repetitive pattern portion within one chip.

2. A pattern inspection method according to claim 1, wherein outputs of said chip comparison inspection and said repetitive pattern comparison inspection are separately introduced into a computer, inspection results obtained by both said comparison inspections are compared with a preset inspection condition within the computer, and only one which exceeds the preset inspection condition is left as the inspection result.

3. A pattern inspection apparatus according to claim 1, wherein the chip comparison inspection inspects a random pattern portion within the chips, to output a defect in the one chip by a first comparator circuit, and the repetitive pattern comparison inspection inspects a repetitive pattern portion to output a defect in the one chip by a second comparator circuit.

4. A pattern inspection apparatus according to claim 3, wherein the detected defect is discriminated if it is a defect by the 2-chip comparison inspection or a defect by the repetitive pattern comparison inspection, which is then displayed or outputted.

5. A pattern inspection method according to claim 3, further comprising:
   scanning the chip patterns with a one-dimensional line sensor;
   supporting the chips on a scanning stage;
   storing data in a memory of a chip comparison inspection region and a repetitive pattern comparison inspection region with respect to a scanning direction of the line sensor and a scanning direction of the stage based on an inspection starting point and predetermined pattern information of a chip;
   and controlling an output of one of a defect output of the chip comparison inspection in a defect output of the repetitive pattern comparison inspection in synchronization with a scanning position of the line sensor and a scanning position of the stage.

6. A pattern inspection apparatus comprising a first comparator circuit for comparing patterns of two chips adjacent to each other on a body to be inspected and a second comparator circuit for comparing the same patterns of the same repetitive pattern portion within one chip, both said comparator circuits capable of being operated in parallel.

7. A pattern inspection apparatus according to claim 6, further comprising a one-dimensional optical line sensor for scanning the chips, whereby a detection of a defect is carried out while continuously scanning a stage supporting the chips.

8. A pattern inspection apparatus according to claim 7, further comprising means for independently setting a defect determination condition of the 2-chip comparison and a defect determination condition of the repetitive pattern comparison.

9. A pattern inspection apparatus according to claim 7, wherein the detected defect is discriminated if it is a defect by the 2-chip comparison inspection or a defect by the repetitive pattern comparison inspection, which is then displayed or outputted.

10. A pattern inspection apparatus according to claim 7, further comprising:
    a one-dimensional line sensor for scanning the chip patterns;
    a scanning stage for supporting the chips;
    a memory for storing data of a chip comparison inspection region and a repetitive pattern comparison inspection region with respect to a scanning direction of the line sensor and a scanning direction of the stage based on an inspection starting point and predetermined pattern arrangement information of a chip; and
    means for controlling an output of one of a defect output of the 2-chip comparison inspection and a defect output of the repetitive pattern comparison inspection in synchronization with a scanning position of the line sensor and a scanning position of the stage.

11. A pattern inspection apparatus according to claim 6, wherein the detected defect is discriminated if it is a defect by the 2-chip comparison inspection or a defect by the repetitive pattern comparison inspection, which is then displayed or outputted.

12. A pattern inspection apparatus according to claim 6, further comprising:
    a one-dimensional line sensor for scanning the chip patterns;
    a scanning stage for supporting the chips;
    a memory for storing data of a chip comparison inspection region and a repetitive pattern comparison inspection region with respect to a scanning direction of the line sensor and a scanning direction of the stage based on an inspection starting point and predetermined pattern arrangement information of a chip; and
    means for controlling an output of one of a defect output of the 2-chip comparison inspection and a defect output of the repetitive pattern comparison inspection in synchronization with a scanning position of the line sensor and a scanning position of the stage.

13. A chip pattern inspection apparatus having a light source for directing light onto the surface of a wafer and having a plurality of chips detecting the light reflected therefrom with a sensor, wherein a sensor signal output from the sensor is processed to obtain an inspection result, comprising:
    a first circuit receiving the sensor signal for comparing the sensor signals of first and second chips with each other, including a first delay memory for storing the sensor signals of the first chip and a comparator for comparing the sensor signals for the first chip stored in said first delay memory with the sensor signals of the second chip received from said sensor during an inspection of said second chip, said comparator providing a first difference output, and a first threshold circuit receiving said first difference output for comparing the first difference output with a first threshold value and providing first circuit output exceeding said threshold value;
    a second circuit receiving the sensor signal including a repetitive pattern delay memory for storing the sensor signal for one of the chips, a comparator for comparing the sensor signal received during an inspection of the same one chip with the sensor signal stored in the repetitive delay memory, said comparator providing a second difference output, and a second threshold circuit receiving said second difference output for comparing the second difference output with a second threshold value to provide an output that exceeds said second threshold value;
    an output control circuit for selecting one of the outputs of said first and second circuits on the basis of a relative position of said sensor with respect to a chip during an inspection, wherein the output selected is provided as the inspection result.

14. An apparatus for chip inspection according to claim 13, further including said first and second threshold circuits each having threshold registers for holding the first and second threshold values, respectively, and means for setting the first and second threshold values in the respective first and second threshold registers in accordance with predetermined information regarding a chip being inspected.

15. An apparatus for a chip inspection according to claim 13, further including first and second defect size determination circuits for respectively receiving the output of the first and second threshold circuits under control of said output control circuit, each said defect size determination circuit having a defect size setting register that holds a defect size value wherein each of said defect size determination circuits compares the respective output of said first and second threshold circuits with the respective defect size setting values to provide an output signal exceeding the defect size setting values, respectively, as the inspection result for each of the first and second circuits.

16. The apparatus for chip inspection according to claim 13, wherein said sensor for detecting light is a one dimensional line sensor and a chip being inspected is supported on a stage; and said output control circuit having an inspection region determination circuit that provides the selection of the output of one of said first and second circuits in accordance with bit position information relating to a scanning position of said line sensor and coordinate position information relating to a relative position between said line sensor and the stage.

17. A chip inspection apparatus according to claim 16 wherein said inspection region determination circuit includes an inspection propriety bit memory and an inspection propriety region data memory for each of said first and second circuits, said inspection propriety bit memories receiving the bit position information regarding said line sensor and said inspection propriety region data memories receiving the coordinate information regarding said stage, each of said inspection propriety memories comparing the respectively received bit position and coordinate information to a plurality predetermined stored region information characteristic of different inspecting regions on a chip being inspected and outputting a signal representative of whether the respective bit position of the line sensor and coordinate position of the stage, respectively, is within one of the inspection regions.

* * * * *